United States Patent
Patriksson

(10) Patent No.: US 9,302,752 B2
(45) Date of Patent: Apr. 5, 2016

(54) BREATHING SENSING DEVICE WITH PRESSURE CHAMBERS HAVING DIFFERENT CROSS-SECTIONAL PASSAGES CONNECTED TO A SYSTEM PRESSURE FOR DETECTING PRESSURE DROP DUE TO BREATHING

(75) Inventor: Ola Patriksson, Karlstad (SE)

(73) Assignee: CONSENSUM AS, Honefoss (NO)

( * ) Notice: Subject to any disclaimer, the term of this patent is extended or adjusted under 35 U.S.C. 154(b) by 652 days.

(21) Appl. No.: 13/581,631

(22) PCT Filed: Mar. 2, 2011

(86) PCT No.: PCT/SE2011/050237
§ 371 (c)(1),
(2), (4) Date: Nov. 5, 2012

(87) PCT Pub. No.: WO2011/108985
PCT Pub. Date: Sep. 9, 2011

(65) Prior Publication Data
US 2013/0066227 A1    Mar. 14, 2013

(30) Foreign Application Priority Data
Mar. 5, 2010  (SE) ......................... 1050211

(51) Int. Cl.
G01F 1/34     (2006.01)
B63C 11/22    (2006.01)
A61B 5/087    (2006.01)
A62B 9/02     (2006.01)

(52) U.S. Cl.
CPC ................. *B63C 11/22* (2013.01); *A61B 5/087* (2013.01); *A62B 9/022* (2013.01)

(58) Field of Classification Search
None
See application file for complete search history.

(56) References Cited

U.S. PATENT DOCUMENTS

| 3,147,499 | A | 9/1964  | Nelson        |
| 3,798,629 | A | 3/1974  | De La Taillade |
| 3,898,705 | A | 8/1975  | Schuler       |
| 4,176,418 | A | 12/1979 | Scott         |
| 5,791,956 | A | 8/1998  | Smith         |

(Continued)

FOREIGN PATENT DOCUMENTS

| CN | 2191176   | 3/1995 |
| CN | 101346273 | 1/2009 |

(Continued)

OTHER PUBLICATIONS

International Search Report and Written Opinion mailed Mar. 28, 2011 in parent PCT application.

(Continued)

*Primary Examiner* — Harshad R Patel
(74) *Attorney, Agent, or Firm* — Jeffrey S. Melcher; Menelli Selter PLLC

(57) ABSTRACT

This invention relates to a breathing sensing device for detecting a pressure drop due to breathing. The device includes a diaphragm (100) having a first pressure chamber (120) on one side and a second pressure chamber (121) on a second side within an actuator housing. The first and second pressure chambers (120,121) are connected to a system pressure (L1) by flow passages (143, 153) having different cross sectional passage area ($A_r$, $A_f$) arranged to facilitate detection of a pressure drop due to breathing.

11 Claims, 9 Drawing Sheets

(56) References Cited

U.S. PATENT DOCUMENTS

2009/0217927 A1    9/2009    Stood
2009/0283155 A1*  11/2009  Yoshino et al. ............ 137/487.5
2012/0321717 A1*  12/2012  Staniforth et al. ............ 424/490

FOREIGN PATENT DOCUMENTS

| EP | 0034569 | A2 | 8/1981 |
|----|---------|----|----|
| EP | 0278598 |    | 8/1998 |
| FR | 2741853 | A1 | 6/1997 |
| WO | 2007/058615 | A1 | 5/2007 |
| WO | 2008/143581 | A1 | 11/2008 |

OTHER PUBLICATIONS

Final Office Action issued in Chinese Patent application No. 2012-556043, pp. 1-4.

Examination Report issued in Australian Patent application No. 2011221621, Mar. 17, 2014, pp. 1-4.

Examination Report issued in Chinese Patent application No. 2014093001244540, Oct. 10, 2014, pp. 1-7.

Office Action issued in Chinese Patent application No. 201180022463.2, Jul. 22, 2015, pp. 1-3.

* cited by examiner

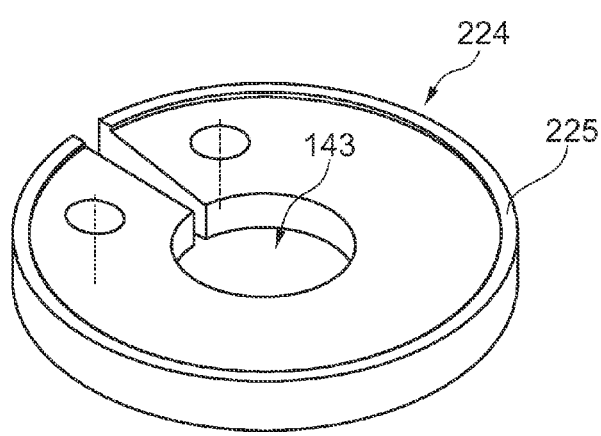
Fig. 3C
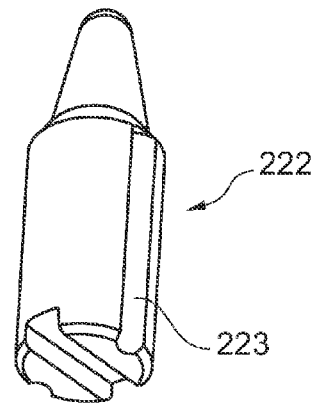
Fig. 3B
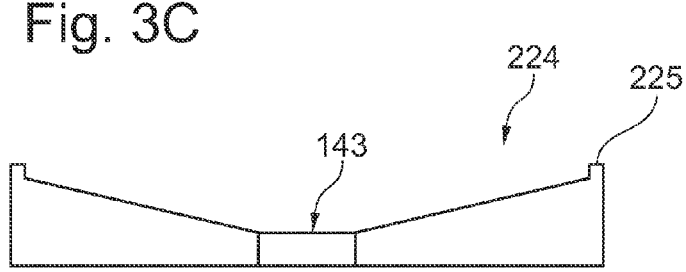
Fig. 3D
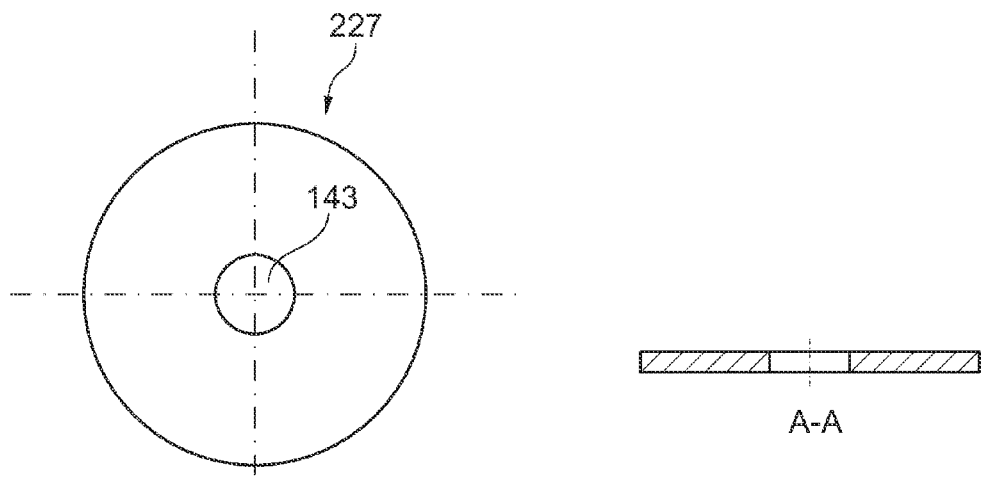
Fig. 3E
Fig. 3F

US 9,302,752 B2

BREATHING SENSING DEVICE WITH PRESSURE CHAMBERS HAVING DIFFERENT CROSS-SECTIONAL PASSAGES CONNECTED TO A SYSTEM PRESSURE FOR DETECTING PRESSURE DROP DUE TO BREATHING

TECHNICAL FIELD

Breathing sensing device, comprising a diaphragm having a first pressure chamber on one side and a second pressure chamber on a second side, wherein said first and second pressure chambers are connected to a system pressure by means of flow passages having different cross sectional passage area arranged to facilitate detection of a pressure drop due to breathing.

BACKGROUND ART

In skin diving with dive tanks, so called SCUBA diving (Self Contained Underwater Breathing Apparatus), the diver is provided with air from pressure tanks that he carries with him during the dive. For obvious reasons it is extremely important that the diving takes place in an appropriate way in order for accidents not to occur. Most persons that plan to dive choose to participate in training before starting to dive for real. Throughout the years, many appliances have been developed in order to prevent accidents in connection with diving. One example is the inflatable diving jacket carried by the diver, which helps him to control buoyancy and which is used in combination with weights in order to help the diver to descend. Examples of other appliances are tables and portable dive computers that help the divers to plan diving in order not to risk the bends or having to surface quickly because air is running out e.g. The diving equipment itself has also developed and has been provided with devices that aim to prevent accidents. Most of these devices have the object of sensing any problems arising or to facilitate for the diver during a dive.

One situation that quite frequently results in near-accidents and sometimes in drowning is when the diver for some reason is suffering from stress as he surfaces. Numerous safety devices in connection with diving equipment are previously known, which intend to give improvement in respect of the shortcomings described above, e.g. FR 2741853 EP 034569, U.S. Pat. No. 4,176,418, U.S. Pat. No. 5,746,543 and U.S. Pat. No. 5,560,738 which all present some disadvantage/s.

Rather recently there has been presented a concept that provides an elegant conceptual solution, disclosed in WO2008143581 and WO2007058615. However also in relation to that disclosure there is room for improvement that may increase safety even more and/or improve cost efficiency and/or improve reliability, etc.

DISCLOSURE OF THE INVENTION

It is an object of the invention to provide a breathing sensing device, especially in connection with the diving equipment, that provides higher reliability and scalability in relation to production aspects, which is achieved by means of breathing sensing device in accordance with claim 1.

Thanks to the invention there is provided design parameters that will allow for scalable production and maintaining high reliability.

According to one aspect of the invention the breathing sensing device comprises a diaphragm having a first pressure chamber on one side and a second pressure chamber on a second side, wherein said first and second pressure chambers are connected to a system pressure by means of flow passages having different cross sectional passage areas arranged to facilitate detection of a pressure drop due to breathing. Said cross sectional passage areas of said flow passages are preferably arranged to be constant through a pressure change in said system pressure $L1$. The relation of cross sectional passage area between the cross sectional passage area providing a restricted flow passages to and/or from second pressure chamber is in the range of $1/50$-$1/200$ in relation to the cross sectional passage area providing a flow passage to and/or from the first pressure chamber, Thanks to the design according to the invention there is acquired a momentary pressure difference between said first and second pressure chambers as a consequence of a pressure change in said system pressure.

According to a further aspect of the invention it is provided that between said second pressure chamber and the system pressure, there is a arranged a further, sealed through passage, having a seal arranged to open said passage above a pressure drop that exceeds a pressure drop that may caused by breathing within said system pressure, wherein preferably $\Delta p_{open} > 3$ bar, more preferred 4 bar, which provides the advantage that the breathing sensing device will not be exposed to undesired forces in relation to sudden pressure increases within the system, e.g. when connecting a new pressure vessel to a diving system.

According to further aspect it is provided that also the height of said pressure chambers is limited to provide compactness, and that a sufficient volume in communication with the second pressure chamber is achieved by arranging at least one additional distributed chamber in connection with said second pressure chamber which provides the advantage that the balancing volume needed for reliable sensitivity of the breathing device is maintained also if the system pressure changes, e.g. in connection with moving up and down in water of a diver, and at the same time provide a compactness of the actuator device itself, due to the fact that the relatively large volume is needed to achieve desired reliability. Hence if all of that volume needed is placed within the balancing pressure chamber itself, it will lead to a bulky unit.

According to further aspect of the invention it is provided that at least one of said passages is adjustably arranged, which provides the advantages that the sensitivity of the breathing sensing device may be adjusted in accordance with different desires. According to further aspect of the invention it is provided that a piston is fixedly connected to said diaphragm, said piston having a an end portion interacting with a seal, which provides the advantage that the diaphragm with the piston unit may be used to operate devices within the unit using the breathing sensing device.

According to further aspect of the invention it is provided that in at least the end portion of the piston there is arranged a coaxial passage arranged to allow through flow when said end portion is out of sealed contact with said seal which provides the advantage of increased possibility of compactness of an actuator unit using a breathing sensing device in accordance with the invention.

According to further aspects of the invention it is provided that at least said end portion of said piston is arranged to provide a balanced configuration in relation to the surrounding pressure influence, which provides the advantage that the breathing sensing device will not be affected by pressure differences acting on a piston connected to the diaphragm.

According to further aspect of the invention it is provided that said piston is arranged to provide an area difference exposing a larger area of the diaphragm in the first pressure chamber than the area exposed in the second pressure chamber, which provides the advantage that a continuous force will be applied across the diaphragm in a closing direction also when the pressure in both pressure chambers are equal.

BRIEF DESCRIPTION OF THE FIGURES

In the following the invention will be described with reference to the appended drawings, wherein.

DETAILED DESCRIPTION

The foregoing aspects and many of the attendant advantages of this invention will become more readily appreciated as the same become better understood by reference to the following detailed description, when taken in conjunction with the accompanying drawings. Further, the description, and the examples contained therein, are provided for the purpose of describing and illustrating certain embodiments of the invention only and are not intended to limit the scope of the invention in any way.

Figure 1:
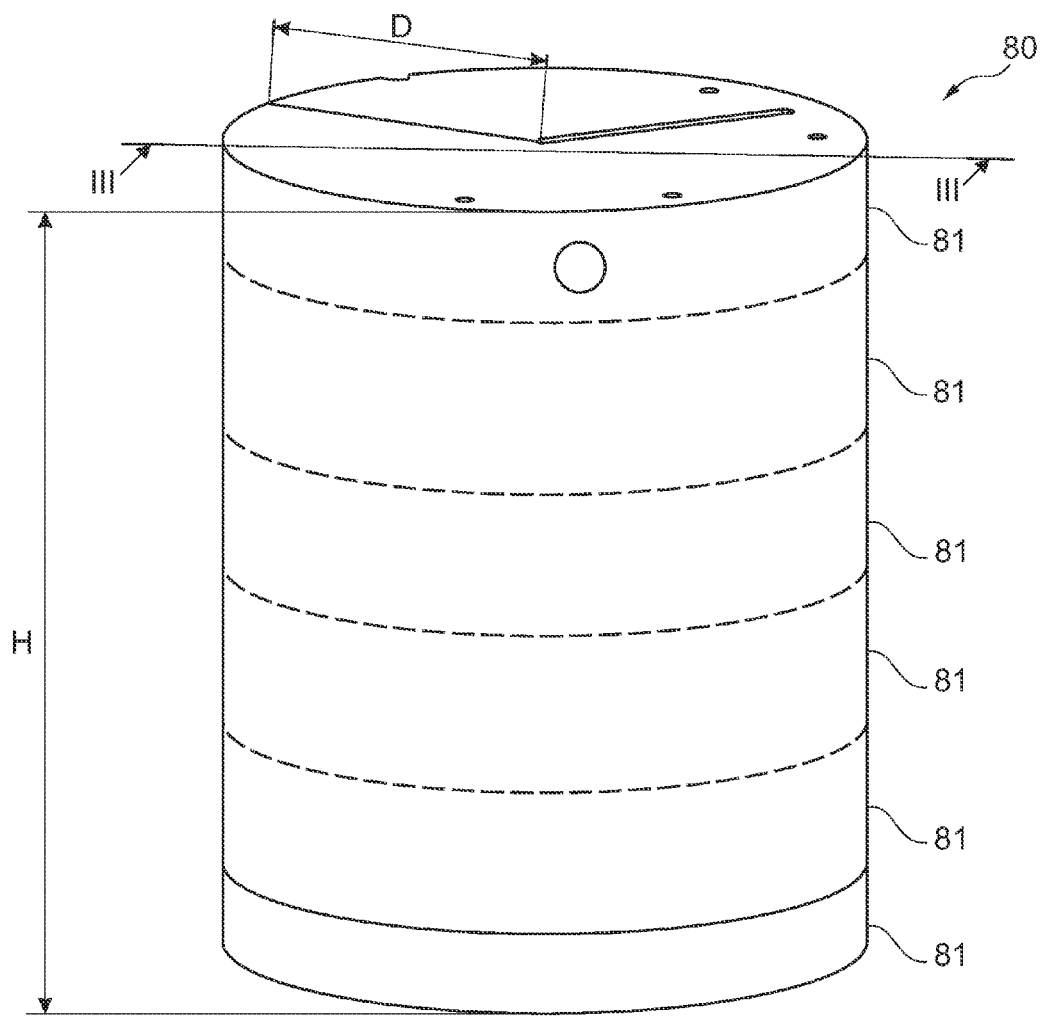
FIG. 1 shows a perspective view of an actuator housing containing different aspects in accordance with the invention.

FIG. 1 shows a perspective view of an actuator housing 80 which housing contains in different aspects in accordance with the invention, which aspects will hereinafter be described in more detail. It is understood that the housing 80 in FIG. 1 is presented for exemplifying reasons and that it may comprises any shape or design, as long as the different aspects and thereto pertaining functions can be achieved within said housing 80. The particular housing shown in FIG. 1 has a cylindrical shape and comprises a number of abutting segments 81 which have been connected together to form said housing 80. Each segment 81 may be designed separately prior to assembly into said housing 80 leading to great manufacturing advantages since every segment 81 can easily be provided with the desired details (e.g. bores, sealings, pressure chambers, diaphragms etc.) before being put together to form an actuator device 8.

Figure 2:
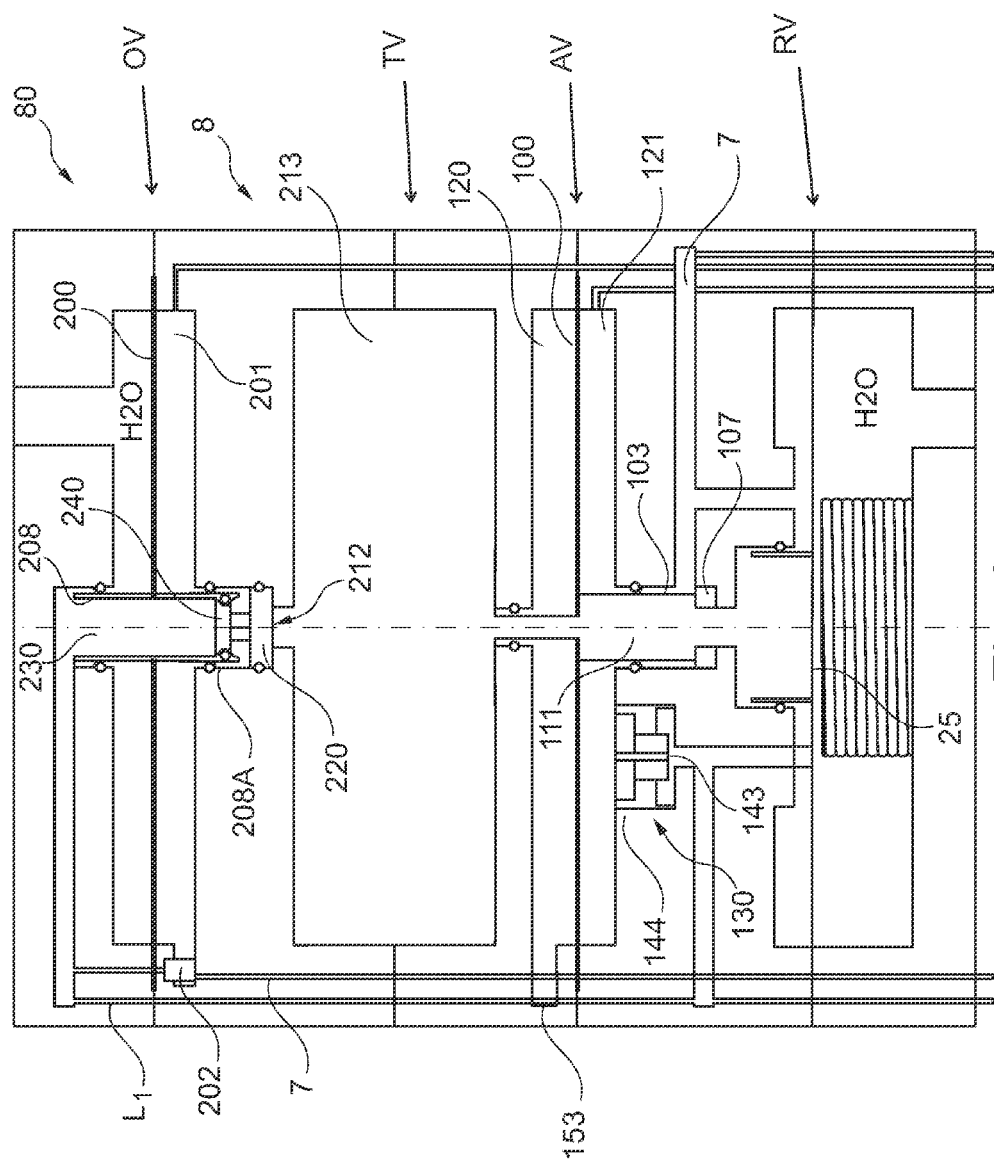
FIG. 2 presents a cross sectional view of an actuator housing along line III-III in FIG. 1, schematically showing the different aspects of the invention.

In FIG. 2 there is shown, in cross section, a schematic view of one embodiment of an actuator 8 in accordance with the invention wherein a compact design of an actuator 8 in accordance with a specific aspect of the invention is achieved. Within the housing 80 there are arranged channels LI connected to the supply pressure of oxygen from the first stage (not shown) and channels 7 connected to ambient pressure. These channels LI, 7 are interconnect via a number of mechanical valves arranged in the housing 80 to fulfill the functionality in accordance with the invention, as will be described in detail below. Adjacent a first end of the actuator housing 80 there is arranged a diaphragm 200 of an ON/OFF valve OV. This valve OV has to be affected by water pressure to be activated into the "on mode". This is achieved by means of the water pressure acting on an outer side of the diaphragm 200. The other side of the diaphragm 200 is balanced by air chamber 201 that is calibrated to allow the diaphragm to move into active state at the desired calibrated pressure. Before applying system pressure (i.e. by connecting the actuator 8 to a first stage of a diving regulator) air chamber 201 is open towards the atmosphere via a valve 202 and channel 7 hereby being in connection with ambient pressure. Once system pressure is applied (air tank is opened), air will flow through channel LI and said valve 202 is affected to move into a closed position, thereby closing the interface between the environment and the chamber 201 underneath the diaphragm 200. The air chamber 201 is thus hermetically closed, and calibrated to the environmental pressure at the surface.

Accordingly, when the water pressure acting on the diaphragm 200 exceeds a certain pressure, a piston 208 fixedly attached to the diaphragm will move downwards into contact with a seal 220 and thereby open up connection to the hollow channel 230 within the piston 208 to a restriction passage 212 leading to a timer volume 213, which is achieved by means of grooves (not shown) on the inner wall of the piston 208, above the inactive position of the seal of sealing body 240 within the hollow channel 230. Hence, when inactive (neutral diaphragm 200) the body 240 seals, but when active (diaphragm 200 and piston 208 move downwards) air will pass by the body 240. The timer volume 213 will hereby slowly be filled in order to gradually build up the pressure therein. The restriction passage 212 is preferably extremely small to allow the actuator body to be very compact. In other words a very little flow of air through the restriction 212 should be allowed, to provide sufficient time for the small volume 213 to achieve the function of the timer volume 213, i.e. opening up the release valve 25 when no breathing has occurred for a predetermined amount of time. The timer volume 213 is positioned next to the on/off valve OV. The release valve 25 is positioned adjacent the opposite end of the actuator body compared to the ON/OFF valve OV.

Between the release valve, RV, and the timer volume, TV, there is arranged the activity sensor valve, AV. This valve AV also comprises a diaphragm 100 having a piston 103 fixedly attached thereto. The piston 103 has a seal, for example an upper lip seal, arranged to seal against flow towards the timer volume TV. Also the piston valve of the AV is hollow, i.e. provides a central passage 111. On one side of the diaphragm 100 there is a pressure chamber 120 in contact with the system pressure line L1. Below, on the other side of the diaphragm 100, there is a pressure chamber 121 providing a balancing pressure. The flow connection opening 153 between the upper chamber 120 and the system pressure L1 is rather large, e.g. to about 2 mm/diameter to allow unrestricted flow there between. The balancing pressure in the lower chamber 121 is achieved by providing a flow restriction arrangement 130 with a restricted passage 143 between the system pressure L1 and the lower pressure chamber 121. In one aspect the restriction passage 143 is combined with a kind of check valve functionality that is obtained by means of e.g. a lip seal 144, as shown in FIG. 2. The skilled person understands that it is also possible to use other types of flow restriction arrangement 130, whereof two examples will be described in connection to FIGS. 3 and 6 respectively.

Figure 6:
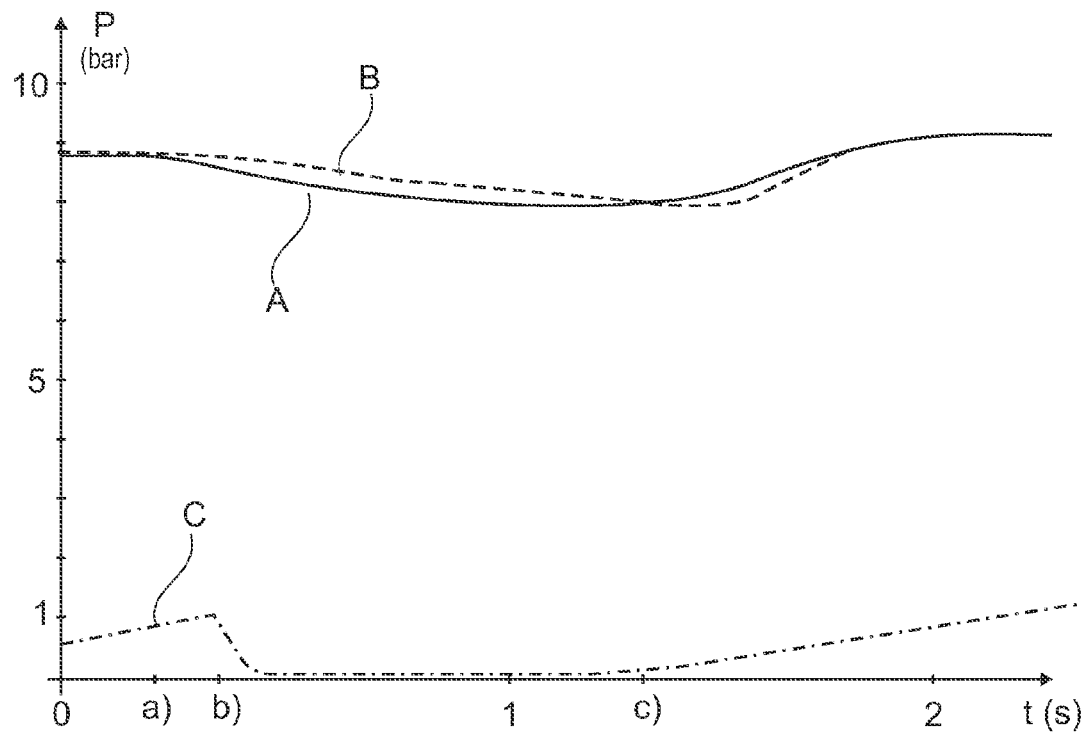
FIG. 6 presents a diagram schematically presenting pressure development over a time in the pressure chambers around a diaphragm and in the timer volume chamber within the breathing sensor arrangement.
Figure 7:
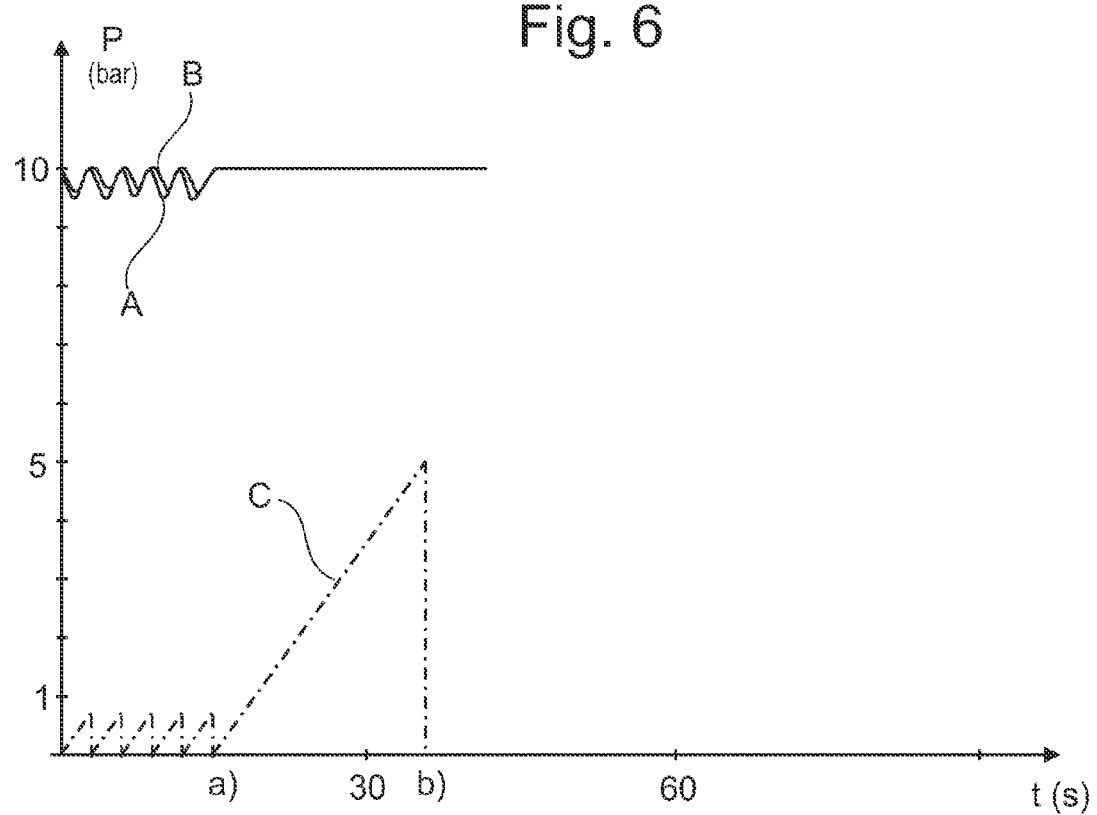
FIG. 7 presents a corresponding diagram as in FIG. 6, showing a different scenario compared to the one presented in FIG. 6, and FIGS. 8A-B show a preferred embodiment of a new kind of diaphragm.

Thanks to this design the AV will empty the timer volume 213 in connection with sensing of a breathing. The pressure development inside the pressure chambers 120, 121 around the diaphragm 100 as well as within the TV chamber 213 will now be described with reference to the details of FIG. 2 and the diagrams presented in FIGS. 6-7. In FIGS. 6-7 graph A is the pressure inside upper pressure chamber 120 over time and graph B shows the pressure inside lower pressure chamber 121 over time. Graph C in FIGS. 6-7 represents the pressure inside timer volume chamber 213 over time.

In brief, when a breathing occurs (see time point a) in FIG. 6) the system pressure LI will suddenly drop and thereby simultaneously provide a pressure drop in the upper chamber 120 (see graph A in FIGS. 6-7). However, the lower chamber 121 (see graph B in FIGS. 6-7) will maintain a higher pressure for a while thanks to the restriction passage 143. As a consequence the diaphragm 100 will move upwardly and thereby the piston 103 will move up from the seat 107, to interconnect the timer volume 213 with ambient pressure by the channel 7 (see time point b) in FIG. 6). When the system pressure slowly again increases, the opposite phenomena will occur, i.e. for a while lower pressure will occur in the lower chamber 121 thereby safeguarding closing of the piston 103 against the seat 107 (see time point c) in FIG. 6). Consequently, again the timer volume 213 will be closed and sealed to successively fill up pressure via flow through the restriction 212.

Looking at the diagram in FIG. 7, here is seen a scenario where breathing has stopped (time point a), and pressure inside pressure chamber 213 is increasing (graph C) until the release valve RV is opened leading to that pressure in volume chamber 213 is nullified (time point b).

In order to further safeguard the sealing of the piston 103 against the seat 107 the upper portion 103A of the piston 103 preferably has a smaller outer diameter and through passage than the lower portion 103B. Further, the piston 103 is so positioned in relation to the diaphragm 100 that part of the undermost area of the diaphragm 100 is covered by the corresponding lower portion of the piston 103B leading to a reduced pressure area compared to the opposite upper side of the diaphragm 100. Thus, at balanced pressure (i.e. when the pressures inside upper 120 and lower 121 chambers respectively are equal), the difference in pressure area leads to that the diaphragm 100 is biased downwards pushing the piston 103 against the seat 107.

There is preferably a lip seal 144 around the AV restriction 130, which lip seal 144 will open up when there is major (and sudden) increase of the system pressure L1, e.g. in connection with change of pressure vessel. Accordingly the lip seal 144 always seals in the direction from the lower pressure chamber 121 to the system pressure L1, but may open in the other direction if the pressure difference between the supply line L1 and the lower chamber 121 exceed a certain level, e.g. 2 bars. Thanks to this arrangement the diaphragm 100 will not be exposed to any major pressure differences, at the same time as the chosen pressure level of opening of the lip seal 144 is chosen such that it may not occur due to the pressure drop provided during breathing.

Figure 3A:
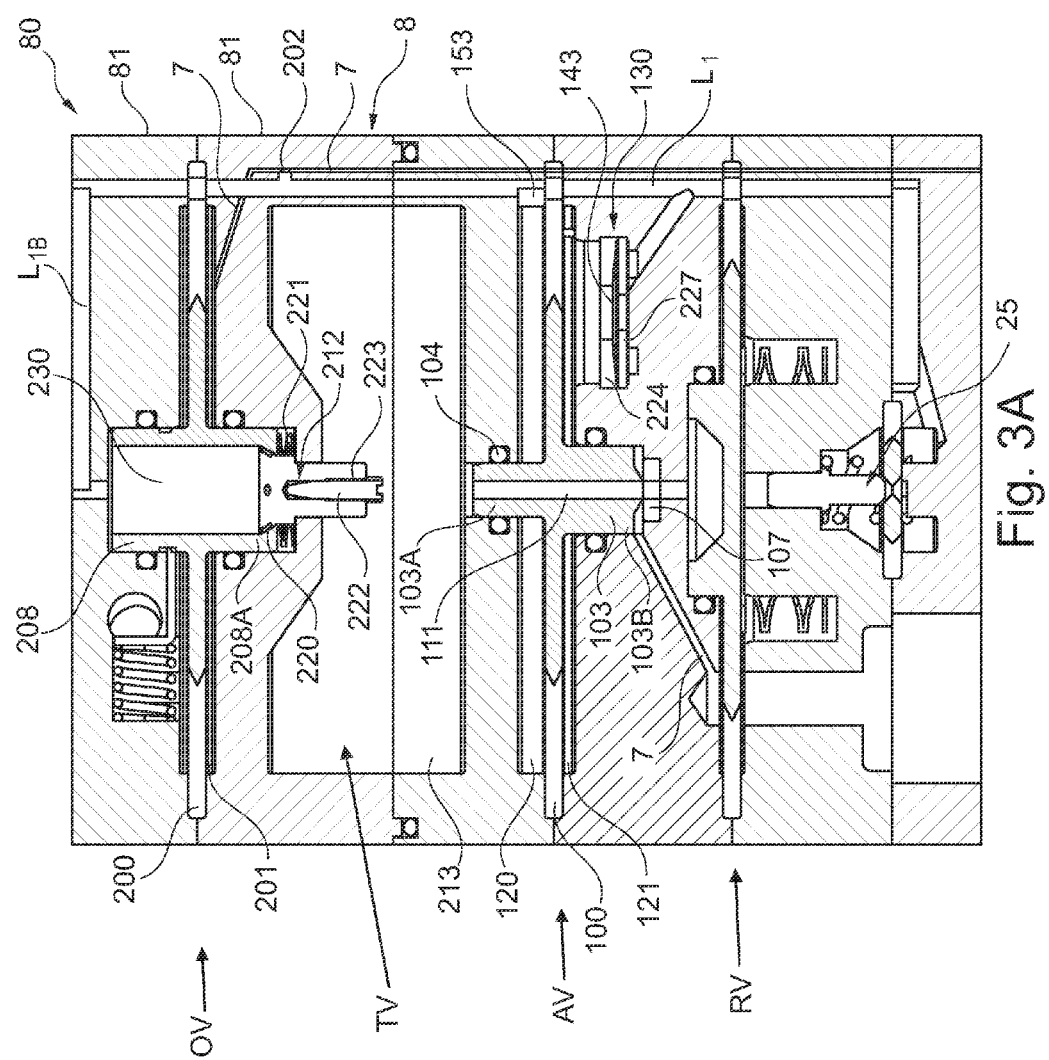
FIG. 3A presents a cross sectional view of an actuator housing along line III-III in FIG. 1, according to another embodiment, schematically showing the different aspects of the invention.

In FIG. 3A there is schematically presented another example of an outline of an actuator assembly 8 according to the invention, comprising the ON/OFF valve OV, timer volume TV, activity sensor valve AV and release valve RV connected to each other in a similar manner to what has previously been described in connection to FIG. 2. The actuator assembly 8 according to FIG. 3 may be contained within a housing 80 corresponding to the one shown in FIG. 1, and is formed by a plurality of housing segments 81 each of which has been designed to fulfill the different functionalities of the actuator 8.

The different aspects and functions of the actuator 8 presented in FIG. 3A will now be described.

In one end of the housing 80 there is arranged an on/off valve OV which is arranged to activate the actuator 8 (i.e. switch it into "on-mode") when the actuator is moved to a position under water and a water pressure is applied onto the upper side of a diaphragm 200. Under the diaphragm 200 there is a balancing air chamber 201 calibrated to allow the diaphragm 200 to move into an active state at a predetermined outer pressure. The diaphragm 200 is also held in position via a spring 221 which is pushing against the under portion of a piston 208 being fixedly attached to the diaphragm 200. In one embodiment the balancing chamber 201 is in contact with the atmosphere via a valve and a channel (not shown) thus automatically being calibrated to ambient pressure until system pressure (i.e. connection to a first step) is applied via channel $L1_B$ whereupon said valve is arranged to close, thereby closing the interface between the environment and the chamber 201 under the diaphragm 200. The air chamber 201 is thus hermetically closed, and calibrated to the environmental pressure at the surface.

When the water pressure acting on the diaphragm 200 exceeds a certain pressure, the piston 208 fixedly attached to the diaphragm will move downwards, pushing against said spring 221, and get into contact with a seal 220 thus preventing unrestricted air passage between $L1_B$ and the timer volume TV 213. The only passage between system pressure channel $L1_B$ is now a restriction passage 212 leading to the timer volume 213, which allows a very small, predetermined airflow to pass through and enter the TV chamber 213. The restriction passage 212 of the present embodiment is achieved by a bar member 222 shown in FIG. 3B. When the diaphragm 200 is in an "off-state" above water the piston 208 will be positioned above the bar member 222 substantially out of contact therewith allowing for air to pass freely through the hollow center channel 230 and passed the bar member 222 into TV chamber 213. When the diaphragm 200 is in an "on-state" under water the piston 208 will move downwards against the bar member 222 sealingly enclosing it and allowing for air passage only through longitudinal grooves 223 arranged on the sides of the bar member 222 (see FIG. 3B). The volume of air passing the restriction valve 212 is hereby determined by the dimension of said grooves 223.

The timer volume 213 will slowly be filled with air and hereby a pressure will gradually be built up therein. The restriction passage 212 is extremely small to allow the actuator body to be very compact. In other words a very little flow of air through the restriction 212 should be allowed, to provide sufficient time for the small volume 213 to achieve the function of the timer volume 213, i.e. opening up the release valve 25 when no breathing has occurred for a predetermined amount of time. The timer volume 213 is positioned next to the ON/OFF valve OV. The release valve 25 is positioned adjacent the opposite end of the actuator body compared to the ON/OFF valve OV.

Between the release valve, RV, and the timer volume, TV, there is arranged the activity sensor valve, AV. This valve AV also comprises a diaphragm 100 having a piston 103 fixedly attached thereto. The piston 103 has an upper seal 104 arranged to seal against flow towards the TV. Also the piston valve of the AV is hollow, i.e. provides a central passage 111. On one side of the diaphragm 100 there is a pressure chamber 120 in contact with the system pressure line L1. Below, on the other side of the diaphragm 100, there is pressure chamber 121 providing a balanced pressure. The flow connection opening 153, preferably a central opening, between the upper chamber 120 and the system pressure L1 is rather large to allow unrestricted flow there between. The balancing pressure in the lower chamber 121 is achieved by providing a flow restriction arrangement 130 with a restricted passage 143 between the system pressure L1 and the lower pressure chamber 121. Preferably said flow passages 143, 153 have different cross sectional passage area $A_r$, $A_f$ arranged to facilitate detection of a pressure drop due to breathing. Preferably the relation of cross sectional passage area between the cross sectional passage area $A_r$ providing a restricted flow passages 143 to and/or from second pressure chamber 121 is in the range of 1/50-1/200 in relation to the cross sectional passage area $A_f$ providing a flow passage to and/or from the first pressure chamber 120. Said cross sectional passage areas $A_r$, $A_f$ of said flow passages 143, 153 are preferably arranged to be constant through a pressure change in said system pressure L1. Thanks to the design according to the invention there is acquired a momentary pressure difference between said first 120 and second 121 pressure chambers as a consequence of a pressure change in said system pressure L1. This will result in that the TV chamber 213 is emptied when a breathing occurs. At a breathing the system pressure L1 will suddenly drop and thereby simultaneously provide a pressure drop in the upper chamber 120. However, the lower chamber 121 will maintain a higher pressure for a while thanks to the restriction passage 143. As a consequence the diaphragm 100 will move upwardly and thereby the piston 103 will move up from the seat 107, to interconnect the timer volume 213 with ambient pressure 7.

Figure 3G:
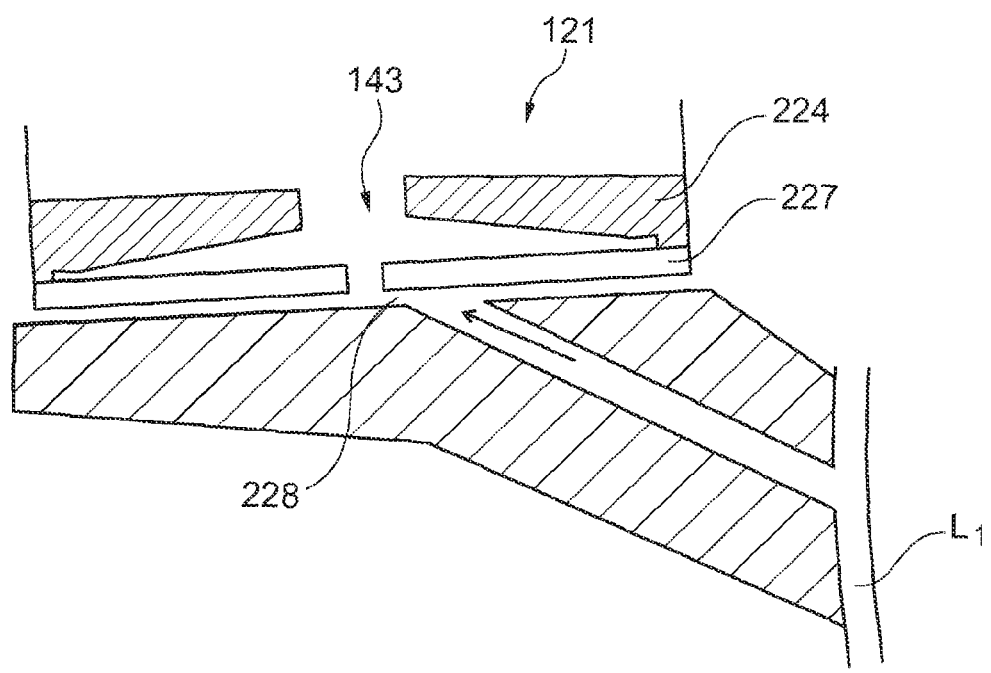
FIG. 3B presents a detail of a valve according the embodiment of FIG. 3A, FIGS. 3C-D present a support plate of a flow restriction valve according to one embodiment of the invention.
FIGS. 3E-F present a flexible member of a flow restriction valve according to one embodiment of the invention, FIG. 3G present a detailed view of a flow restriction valve according to one embodiment of the invention.

The design of the flow restriction arrangement 130 presented in FIG. 3 is now to be further described, referring to FIGS. 3A-G.

A support ring 224 is positioned between the pressure chamber 121 and the system pressure L1, said support ring 224 having a central opening 143 and a circumferential edge 225. The support ring 224 has a beveled cross section, as is also seen for instance in FIG. 3D.

Adjacent to the support ring 224 is positioned a flexible member 227 presented in FIGS. 3E-F, matching the support ring 224 in shape and having a central opening 143. The flexible member is made of rubber, silicone or any other flexible material. In a neutral state (i.e. minimal or no pressure difference between chamber 121 and channel L1) the flexible member 227 will lie horizontally under the support ring 224 and thanks to the beveled cross section of the support ring 224 a small open space is created between the support ring 224 and the flexible member 227. Thus passage 228 leading to channel L1 is uncovered and air may freely move between the chamber 121 and channel L1 through the central opening 143 and via said passage 228 (see FIG. 3G).

The assembly is presents in detail in FIG. 3G, wherein is seen the narrow air flow passage 228 between the flexible member 227 and system pressure channel L1, being the only connection between the pressure chamber 121 and the system L1. A breathing will lead to a sudden pressure drop in the system L1 until the first stage compensates for the pressure fall, referred to as the cracking pressure. When this happens the pressure inside pressure chamber 120 will also fall and air will exit through the flow passage 153 into system channel L1. Simultaneously there will be an initiation of air wanting to pass from the lower pressure chamber 121 into the system channel L1 for compensating the pressure fall. This, however, will lead to that the flexible member 227 gets sucked towards the air flow passage 228, immediately blocking the same so that virtually no air will be able to pass. The result is a pressure difference between the upper 120 and the lower pressure chamber 121, which will lead to that the diaphragm 100 is moved upwards and with it also the piston 103. The piston will thereby leave the contact with the sealing seat 107, allowing for air from the TV chamber 213 to exit through channel 7, and out from the actuator 8. Next, the air from the first stage will enter the system increasing the pressure until pressure in the two pressure chambers 120 and 121 is even, and the flexible member 227 is released thereby opening the restriction valve 130.

In case of gradually increased system pressure, e.g. due to increased water depth upon descent, the flexible member 227 will either not be notably affected, or it will be urged towards the support ring 224, thereby allowing unrestricted air flow between the chamber 121 and channel L1. Thanks to this design, at small or gradual pressure changes the system will be self-regulating and the restriction valve 130 will not block air passage in case of small/slow pressure changes, for instance caused by change of depth within the water. This means that unless a sudden pressure change occurs (such as a breathing) the pressure chambers 120, 121 are automatically equilibrated and adapted to the present system pressure.

In order to safeguard the sealing of the piston 103 against the seat 107 the upper portion 103A of the piston 103 has a smaller outer diameter and through passage than the lower portion 103B. Further, the piston 103 is so positioned in relation to the diaphragm 100 that part of the undermost area of the diaphragm 100 is covered by the corresponding lower portion of the piston 103B leading to a reduced pressure area compared to the opposite side of the diaphragm 100. Thus, at balanced pressure (i.e. when the pressures inside upper 120 and lower 121 chambers respectively are substantially equal), the difference in pressure area leads to that the diaphragm 100 is biased downwards pushing the piston 103 against the seat 107.

In a scenario where a diver has stopped breathing and the volume inside TV chamber 213 will not be emptied by means of the AV valve as described, and the pressure inside TV chamber 213 will gradually increase. At a certain crucial point the increased pressure will lead to opening of the release valve 25 whereby air from the tank will flow into the BCD, inflating the diving jacket.

Figure 4:
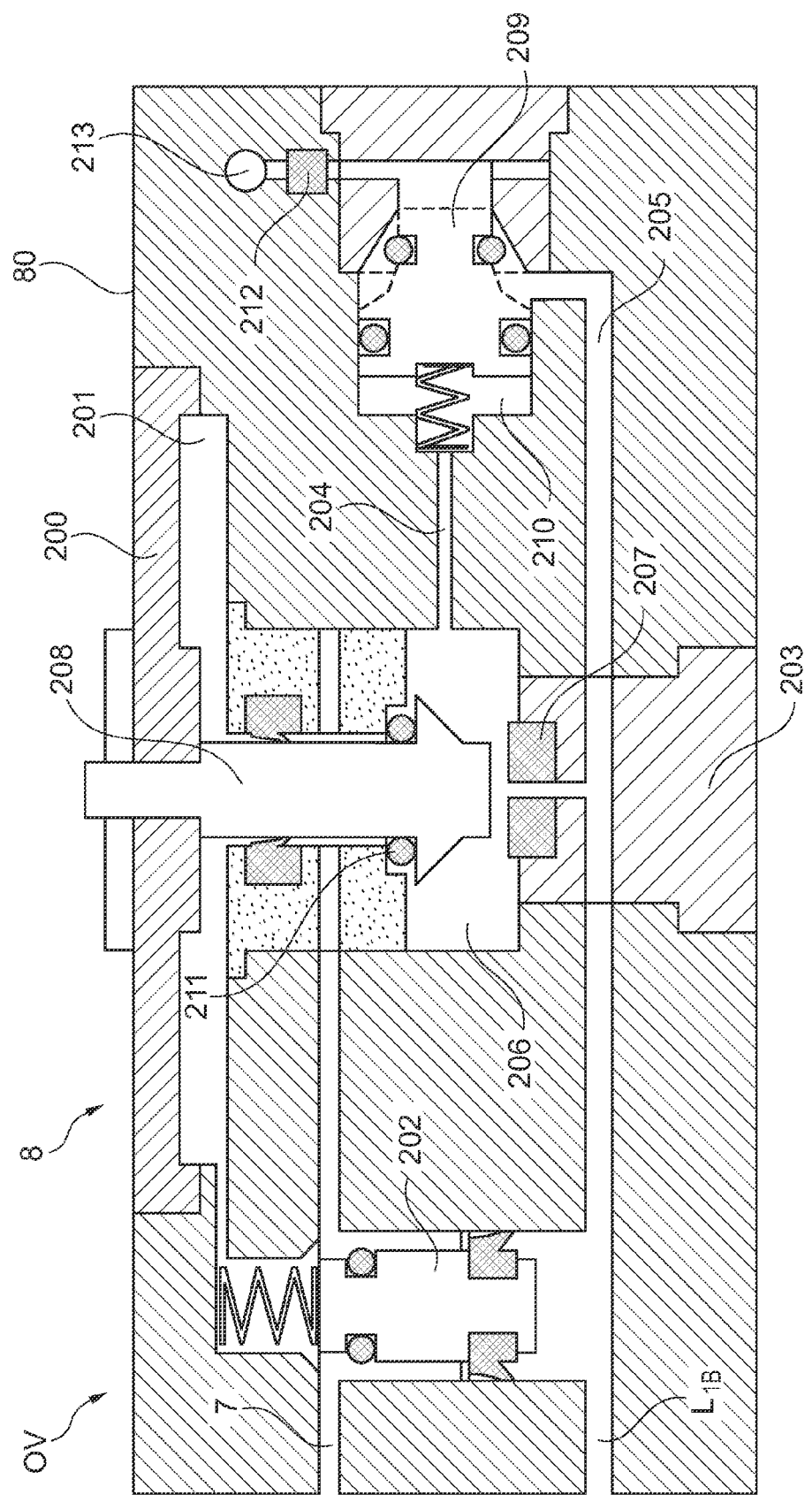
FIG. 4 presents a detailed view of one aspect of the invention according to one embodiment of the invention.
Figure 5:
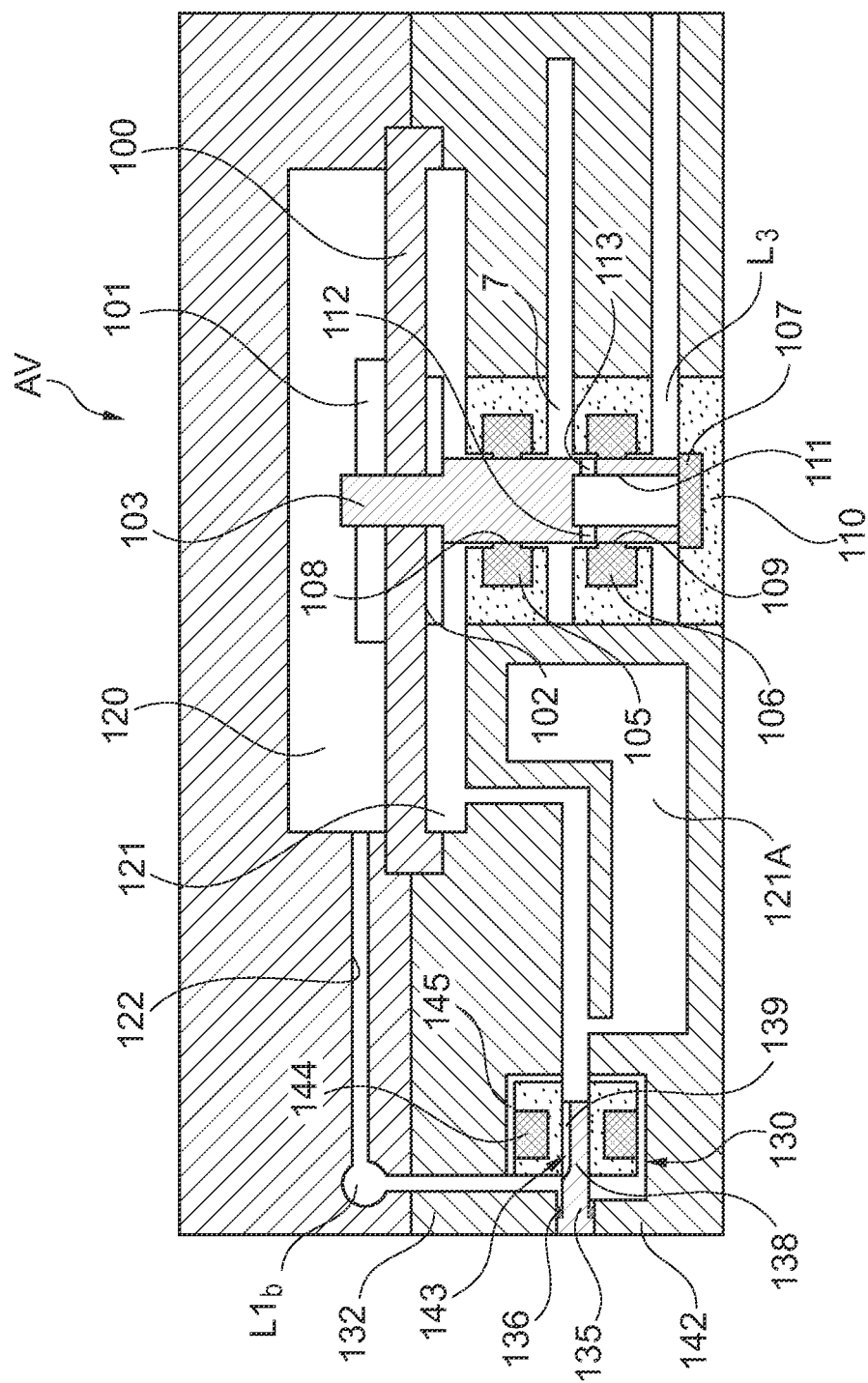
FIG. 5 presents a detailed view of another aspect of the invention according to one embodiment of the invention.

The arrangements presented in FIGS. 4-5 comprise a housing 8 of another type compared to previous embodiments (FIGS. 1-3), having a rectangular shape.

In FIG. 4 there is shown a principle cross-sectional view of an ON/OFF-valve in accordance with the invention, i.e. showing some principles according to one embodiment of a mechanical ON/OFF-valve to be used in an actuator. Calibration of the diaphragm 200 is achieved by having the lower side of the diaphragm 200 connected to ambient pressure via a valve 202 and a channel 7 within the actuator housing, which channel 7 is connected to ambient pressure. When system pressure is applied (a pressure that is always connected to the actuator) the valve 202 will close, by compressing the spring that otherwise will keep the valve 202 open. Hence, the surface area (here at the bottom of the valve 202) provides a sufficient area to counteract that the spring is provided to safely close the valve 202 when system pressure is applied in the channels $L1_B$ connected thereto.

System pressure from $L1_B$ will pass by below the valve 202 further on to the seating unit 203, which divides this flow into two branches, one flow that penetrates through the upper portion 207 of the valve seat 203 into a chamber 206 and one branch that will pass straight through the seat 203 into a further channel 205. A piston 208 is connected to the diaphragm 200, which piston protrudes downwardly in direction towards the centre of the actuator housing 8. The lower portion of the piston 208 penetrates into the chamber 206 that receives the flow from the system pressure line $L1_B$ (as described above). When the diaphragm 200 is in its usual position, i.e. not pressurized by ambient water, the lower portion of the piston 208 will be out of contact with a seal 207 positioned on the seating 203, which facilitates flow from the system pressure line $L1_B$ to the surrounding chamber 206. In the upper part of the chamber 206 there is a channel 204, which will be provided with the system pressure via chamber 206 (when the system is in its upper position) and will supply pressure to one side of a third valve 209 to push that valve 209 in a right hand direction into a closing position. Due to a minor exposed surface of the valve 209 to the lower channel 205 this pressure may not force the valve to an open position.

When the actuator is moved to a position under water and a water pressure is applied, the upper side of the diaphragm 200 will arrange for displacing the piston 208 into contact with the sealing 207 in the seat 203. The piston 208 has then moved out of contact with an upper seal 211 in chamber 206 and has subsequently also closed the connection between system pressure $L1_B$ and pressure chamber. As a consequence pressurised air in channel 204 on the left hand side of the valve 209 may evacuate along the piston shaft upwardly into a channel that is in connection with ambient pressure line 7. As a consequence ambient pressure will then exist in the channel and chamber 210 on the left hand side of the third valve 209. However, the lower channel 205 connected to the third valve 209 is still connected to system pressure $L1_B$ and as a consequence the third valve 209 will move to the left and open up passage that via restriction passage 212 leads to the timer volume 213.

Now referring mainly to FIG. 5 presenting an AV valve and a restriction valve 130 according to one embodiment of the invention.

Two steel plates 101, 102 are compressed around the rubber body of the membrane 100 such that the rubber will expand and seal against the piston 103. Hereby is secured that no air may pass via the piston 103.

A first lip seal 105 has a lip 108 protruding outwardly to provide a sealing from pressure coming from above, but will allow airflow from below. The outer cylindrical surface of the piston 103 is totally even. In the channel 7 below this sealing 105 there exists ambient pressure and accordingly no airflow may pass through upwardly.

A second lip seal 106 is positioned upside down in relation to the first lip seal 105, such that its lip 109 will prevent air from passing along the piston surface upwardly. As with the first seal 105 the "allowing side" of the second seal 106 faces ambient pressure in channel 7.

The bottom end 110 of the piston 103 has a central coaxial hole 111, extending less than half the length of the piston 103. The hole 111 leaves an annular end 110 having a configuration that allows sealing functionality against a bottom rubber sealing 107. Accordingly when the membrane 100 and the piston 103 are in a non activated position, the piston end 110 will seal against the bottom rubber sealing 107. Thanks to the design of the end piece of the piston 103 regarding to the pressure line L3, there will be provided no lifting action on the piston 103 from the pressure applied in L3, i.e. the piston is balanced in relation to pressure in line L3.

When the pressure suddenly drops in the inlet line $L1_b$ the membrane 100 will be affected, providing a lifting force of the membrane 100 (as will be described more in detail below). This will cause the end 110 of the piston 103 to lift upwardly and thereby allow air in L3 to move into the central bore 111 within the piston 103. Thereby there has been established communication between the intermediate channel 7 and perpendicular bores 112, 113 within the piston 103. Since the pressure L3 is always higher than the ambient pressure existing in the intermediate channel 7 air will then "automatically" flow from L3 to the channel 7. This flow will then reset the timer function. Thanks to the positioning of the holes 112, 113 slightly above the lip 109 of the lower seal 106 there is no risk that the edges of the holes 112, 113 will erode/wear any of the sealings 105, 106.

Around the membrane 100 there is arranged an upper chamber 120 and a lower chamber 121. The distance between the membrane and the upper wall of the upper chamber 120, as small as possible, e.g. is about 1.5 mm in order to obtain a housing that is as compact as possible. However, the lower chamber 121, (as will be described more in detail below) needs to provide larger volume than the specific space 121 existing nearby the membrane 100. Therefore there are arranged extra volumes 121A in other positions of the housing main body used for the actuator 8. In other embodiment there may be provided three or more separate chambers in communication to provide a desired extra volume 121A.

In order to obtain a desired functionality by means of the membrane 100 there is a need for very quick response in relation to the airflow in conjunction with breathing of the diver. It is the pressure drop that occurs during breathing that need to be identified. This pressure drop may be about 0.5 bars, normally within 0.2-1.5 bars and need to be sensed independent on which pressure that exists in the supply line $L1_b$. This is a necessity for instance because a diver will move between different depths leading to different pressure levels, etc.

By means of arranging a restriction 143 between the channel $L1_b$ and one of the pressure chambers 121 it is feasible to quickly identify that breathing is initiated. In order to establish a sufficient difference in pressure between the two chambers 120, 121 the reduction of through passage area $A_r$ in connection with the lower pressure chamber 121 need to be in the magnitude of about $\frac{1}{100}$ in relation to the area $A_f$ of the flow passage 153 to the upper chamber 120. At least there is a need of a relation between $\frac{1}{50}$ to $\frac{1}{200}$. In the used embodiment the through hole 122 for allowing free passage of air to the upper chamber has a diameter about two millimeters, and accordingly the diameter of the restricted passage corresponds to about 0.2 mm.

According to the embodiment illustrated in FIG. 5 the flow restriction arrangement 130, that achieves/provides the desired functionality, comprises a bore 131 with a needle valve body 135. The needle valve body 135 is threadidly engaged with the housing 132 and sealed 136. At the front end of the needle valve body 135 there is a front portion 138, that interacts with a seat 142. In the front portion 138 there is arranged tiny groove 139, which provides very fine adjustability for flow of air from the inlet channel $L1_b$ into a channel 141 leading to the lower pressure chamber 121.

Accordingly, when the needle valve 135 is introduced such that all of the groove 139 is behind the seat 142, no air may pass by, i.e. it will then totally seal the circular passage in the seat 142. Then by slightly rotating the body 135, in a opening direction, more and more of the groove 139 will appear providing a larger and larger through passage. Accordingly this provides a very fine calibration of the desired through passage 143 of air from the inlet L1$_b$, such that the size of said passage 143 is within the desired range in relation to the passage to the upper pressure chamber 120. Exteriorly of the seat 142 there is arranged a lip seal 144 which thanks to its resiliency, will allow for through passage of air from L1$_b$ if a certain pressure level is exceeded. For instance in conjunction with attaching the equipment to a new pressure bottle there will be a sudden increase in pressure and accordingly this lip seal 144 will then open up an annular passage 145, to allow air to flow into the lower chamber 121 simultaneously as air/pressure flows into the upper chamber 120.

It is evident for the skilled person that the functionality that has been described above in relation to the restriction arrangement 130 may easily be achieved in various manners without as many details as has been described above. In an extreme embodiment all of it may be included in one single unit just presenting a desired fixed restriction passage 143 in combination with the kind of check valve functionality that is obtained by means of the lip seal 144. Accordingly many variations may be made to the exact design of this arrangement 130.

The function during normal use is such that when the diver breathes the above described small pressure drops will occur in the inlet line L1$_b$. This pressure drop will immediately be communicated to the upper pressure chamber 120. However the lower pressure chamber 121 will not instantly be provided the same pressure due to the restricted passage 143 that connects inlet line L1$_b$ with said pressure chamber 121. Accordingly there will for a moment, (about 20-50 ms) be created a pressure difference over the membrane 100, which in turn will affect the membrane 100 to flex in the direction where the lowest pressure resides. Hence the membrane 100 will move upwardly into the upper chamber 120 and thereby move the piston 103. Thereby the timer release activation will be obtained as described above and the actuator reset.

Figure 8A:
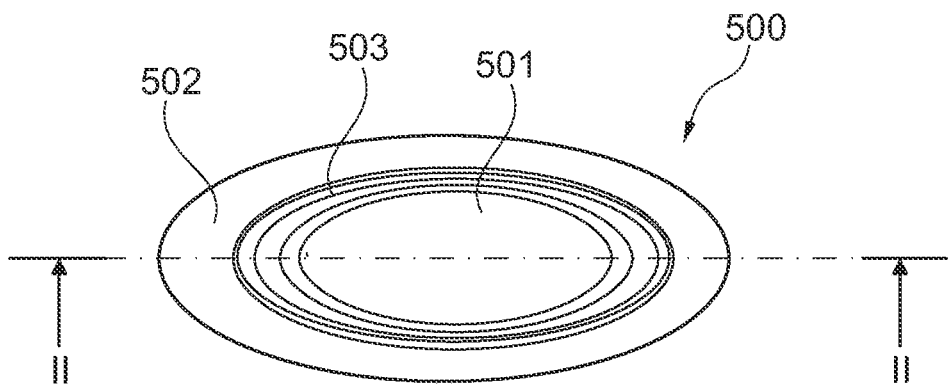
Figure 8B:
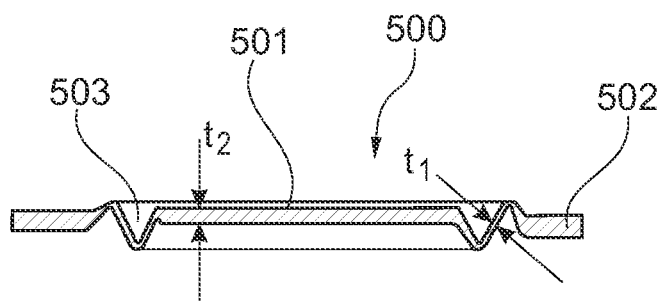

In FIGS. 8A, 8B there are shown a new kind of diaphragm that advantageously may be used together with the other innovative aspects mentioned above, but which diaphragm may also provide advantages when used in other kind of applications, e.g. within engines, different kind of sensors, etc. Accordingly it is foreseen that separate protection in varying fields may be applied for at a later stage, e.g. by means of divisional. In FIG. 8A it is shown that the diaphragm according to the invention comprises a flat shaped body 500. The body 500 has an outer portion 502 arranged to allow fixation of the diaphragm and an inner portion 501, 503 arranged to allow for movement in response to pressure differences sensed by the opposite sides of the inner portion 501, 503. According to the invention (see FIG. 8B) the inner portion 501, 503 comprises a central area 501 and an annular area 503 surrounding the a central area 501, wherein the material thickness t$_1$ of the annular area 503 is substantially smaller than the thickness t$_2$ of the central area 501. The thickness (t$_2$) of the central area 501 is preferably at least two times thicker than the material thickness (t$_1$) of the annular area 503, which will allow for the advantage that the central area is much more rigid than the annular are, which in turn will allow for good control of the movement of the central area 501. According to a preferred embodiment the central area 501 and the annular area 503 are made from the same material, and further indeed also the outer portion 502, which may facilitate cost efficient production. Further the annular area 503 is substantially bellow-shaped according to a preferred embodiment, since this will provide a high degree of flexibility, which is especially favorable if the material used is a relatively stiff metal and/or metal alloy. A further advantage with the use of metals is that desired measures may be achieved by pressing.

The invention claimed is:

1. Breathing sensing actuator comprising:
an actuator housing;
a supply pressure connection constructed to connect the actuator housing to a supply pressure and provide a system pressure within the actuator housing;
a timer chamber defined by the actuator housing, wherein when the actuator is connected to the supply pressure, the timer chamber fills with air from the system pressure through a restriction passage;
a release valve constructed to release air pressure from the timer chamber when an air pressure in the timer chamber reaches a set release pressure value and fill a floatation device with the released air pressure;
an activity valve comprising an activity diaphragm, the activity valve being constructed to release air pressure from the timer chamber when breathing by a diver using the actuator occurs, wherein the restriction passage is constructed to fill the timer chamber at a set rate so that if breathing does not occur by a set time the set release pressure value will be reached and the release valve will open;
a first pressure chamber defined by the actuator housing and a first side of the activity diaphragm and having a first flow passage in communication with the supply pressure and the first pressure chamber;
a second pressure chamber defined by the actuator housing and a second side of the activity diaphragm and having a second flow passage in communication with the supply pressure and the second pressure chamber, wherein when the actuator is connected to the supply pressure said first and second pressure chambers are connected to the system pressure by flow passages having different cross sectional passage areas arranged to facilitate detection of a pressure drop due to breathing, wherein the relation of cross sectional passage area between the cross sectional passage area providing a restricted flow passages to and/or from the second pressure chamber is in the range of 1/50-1/200 in relation to the cross sectional passage area providing a flow passage to and/or from the first pressure chamber, arranged to acquire a momentary pressure difference between said first and second pressure chambers as a consequence of a pressure change in said system pressure.

2. The breathing sensing actuator according to claim 1, further comprising an on-off valve comprising an on-off diaphragm, the on-off diaphragm having a first side contacting an ambient environment and a second side contacting a balance chamber defined by the actuator housing, wherein when water pressure contacting the first side of the on-off diaphragm is greater than a pressure in the balance chamber the actuator is switched into an on mode, and the balance chamber is open to the ambient environment before a system pressure is opened and closed to the ambient environment when the system pressure is opened to calibrate the pressure in the balance chamber to the ambient pressure at a surface of water.

3. A method of breathing while diving comprising:
attaching the actuator according to claim 1 to the supply pressure; and
breathing by a diver under water through the actuator, wherein the activity valve releases pressure from the timer chamber.

4. The method of breathing while diving comprising:
attaching the actuator according to claim 1 to the supply pressure; and breathing by the diver under water through the actuator slower than the set time period and the release valve opening and filling a floatation device to float the diver to a surface of the water.

5. The breathing sensing actuator according to claim 1, wherein said cross sectional passage areas of said flow passages are arranged to be constant through a pressure change in said system pressure.

6. The breathing sensing actuator according to claim 1, wherein between said second pressure chamber and the system pressure a sealed through passage is further arranged having a seal arranged to open said passage above a pressure drop that exceeds a pressure drop that may be caused by breathing of said system pressure.

7. The breathing sensing device according to claim 4, wherein the pressure drop is >3 bar.

8. The breathing sensing device according to claim 4, wherein the pressure drop is >4 bar.

9. The breathing sensing actuator according to claim 1, wherein the height of said pressure chambers is limited to provide compactness, and that a sufficient volume in communication with the second pressure chamber is achieved by arranging at least one additional distributed chamber in connection with said second pressure chamber.

10. The breathing sensing actuator according to claim 1, wherein at least one of said passages is adjustably arranged.

11. The breathing sensing actuator according to claim 1, wherein a piston is fixedly connected to said activity diaphragm, said piston having an end portion interacting with a seal.

* * * * *